US010533974B2

(12) United States Patent
Ishiyama (10) Patent No.: US 10,533,974 B2
(45) Date of Patent: Jan. 14, 2020

(54) LASER MEASURING DEVICE AND LASER ULTRASONIC DEVICE

(71) Applicant: Hitachi, Ltd., Tokyo (JP)

(72) Inventor: Kazuo Ishiyama, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 82 days.

(21) Appl. No.: 15/653,571

(22) Filed: Jul. 19, 2017

(65) Prior Publication Data

US 2018/0080906 A1 Mar. 22, 2018

(30) Foreign Application Priority Data

Sep. 21, 2016 (JP) ................................. 2016-184205

(51) Int. Cl.
*G01B 9/02* (2006.01)
*G01N 29/24* (2006.01)
(Continued)

(52) U.S. Cl.
CPC ....... *G01N 29/2418* (2013.01); *G01N 29/041* (2013.01); *G01N 29/075* (2013.01); *G01N 29/348* (2013.01)

(58) Field of Classification Search
CPC ............. G01N 29/2418; G01N 29/041; G01N 29/075; G01N 29/348; G01B 9/02081; G01B 2290/70
(Continued)

(56) References Cited

U.S. PATENT DOCUMENTS 5,604,592 A * 2/1997 Kotidis .............. G01N 21/1717
356/432
9,188,478 B2 * 11/2015 Pouet ..................... G01H 9/008
(Continued)

FOREIGN PATENT DOCUMENTS

JP      2014-109481 A    6/2014
JP      2014-160057 A    9/2014

OTHER PUBLICATIONS

S. Krishnaswamy. "Theory and Applications of Laser-Ultrasonic Techniques", http://www.cqe.northwestern.edu/sk/SK-Papers/B5_lutchapter_2003.pdf.
(Continued)

*Primary Examiner* — Tarifur R Chowdhury
*Assistant Examiner* — Jonathon Cook
(74) *Attorney, Agent, or Firm* — Mattingly & Malur, PC (57) ABSTRACT

A laser measuring device includes a light source, a first splitter, a second splitter, first photodetection units, and second photodetection units. The light source emits laser light. The first splitter splits the laser light into light to be incident on a specimen and reference light that travels in a predetermined direction. The second splitter is where a combined wave formed by combining signal light reflected off the specimen and the reference light traveling in a direction different from the predetermined direction enters. The first photodetection units detect one part of the combined wave that has been transmitted through the second splitter. The second photodetection units detect another part of the combined wave that has been reflected off the second splitter. The first splitter has an asymmetric splitting ratio set such that power of the reference light becomes larger than power of the light to be incident on the specimen.

14 Claims, 7 Drawing Sheets

(51) Int. Cl.
*G01N 29/04* (2006.01)
*G01N 29/07* (2006.01)
*G01N 29/34* (2006.01)

(58) Field of Classification Search
USPC ................................ 356/477, 482, 493, 498
See application file for complete search history.

(56) References Cited

U.S. PATENT DOCUMENTS

| | | | |
|---|---|---|---|
| 2009/0027688 A1* | 1/2009 | Pouet | G01N 29/2418 356/502 |
| 2014/0152998 A1 | 6/2014 | Okuda | |
| 2014/0204388 A1 | 7/2014 | Osawa et al. | |

OTHER PUBLICATIONS

R. J. Dewhurst, et al., "Optical remote measurement of ultrasound", Meas. Sci. Technol., vol. 10, 1999, pp. 139-168.

Y. K. An., et al., "Complete noncontact laser ultrasonic imaging for automated crack visualization in a plate", Smart Mater. Struct., vol. 22, 2013, pp. 1-10.

\* cited by examiner

LASER MEASURING DEVICE AND LASER ULTRASONIC DEVICE

BACKGROUND OF THE INVENTION

1. Field of the Invention

The present invention relates to a laser measuring device and a laser ultrasonic device.

2. Description of the Related Art

Generally, laser ultrasonics allows non-contact measurement of a specimen in principle. Laser ultrasonics is, therefore, suitable when contact with the specimen is difficult, for example when the specimen is at high temperature, high altitude, in a high radiation field, of a small size or complicated shape, or when the specimen needs to be measured by remote control due to poor proximity. Due to such characteristics, laser ultrasonics is expected to be applied to various fields (for example, refer to S. Krishnaswamy. "Theory and Applications of Laser-Ultrasonic Techniques", http://www-.cqe.northwestern.edu/sk/SK-Papers/B5_lutchapter_2003.pdf).

Upon transmitting ultrasound by a laser, a specimen is irradiated with pulsed laser light (transmission laser) in time. When the power density of the laser light is low, thermal stress is generated through a rapid heating and cooling process on a micro region of the surface. The generated thermal stress then becomes a source of distortion of the material, generating an ultrasonic signal (a thermoelastic mode).

By contrast, when the power density of the laser light is high, a target surface layer of the specimen is turned into plasma, generating vibration (an ablation mode) by the pressure applied to the specimen as a reaction to the expansion of plasma.

For the reception of ultrasound by a laser, a technique for detecting the surface displacement or the velocity of vibration at a reception point induced by the ultrasound is employed. This technique utilizes the coherence of laser light (reception laser) for the ultrasound reception. As methods for detecting ultrasonic signals by a laser, a Michelson interferometer, a Fabry-Perot interferometer, an interferometer using a phase conjugate optical element, a knife edge technique, and the like has been proposed (for example, refer to R. J. Dewhurst, et al., "Optical remote measurement of ultrasound", Meas. Sci. Technol., vol. 10, pp. 139-168 (1999)). By combining these laser ultrasonic transmission and reception techniques, it is possible to realize laser ultrasonics, which is a non-contact ultrasonic transmission and reception method.

Techniques related thereto include JP-2014-109481-A and JP-2014-160057-A, for example.

SUMMARY OF THE INVENTION

For the nondestructive measurement, the laser ultrasonics described above needs to be in the thermoelastic mode, and thus a transmission signal is small. Furthermore, the reception sensitivity of a receiver using a laser interferometer is lower than the reception sensitivity of a contact-type sensor. A drawback of the laser ultrasonics is, therefore, that the measurement sensitivity thereof is low, compared with a case where a contact-type ultrasonic sensor is used for normal transmission and reception.

To overcome this drawback, increasing the laser power of the reception laser can be an option. However, this poses a concern that increasing the laser power of the reception laser may generate new ultrasound by the reception laser or damage an optical fiber if an optical fiber probe is used.

Figure 1:
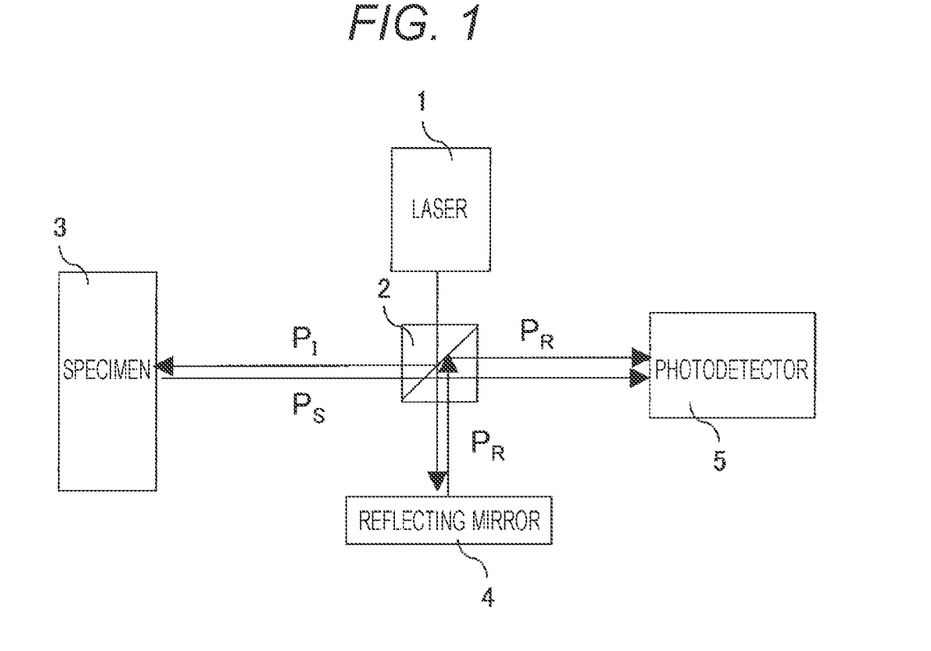
FIG. 1 is a schematic diagram illustrating a Michelson interferometer as a related art.

In a laser receiving system including a Michelson interferometer (refer to FIG. 1) or an interferometer using a phase conjugate optical element, the phase change $\Phi_{UT}(t)$ due to the displacement induced by the ultrasound in a specimen is converted into a signal intensity I(t) as expressed by the following equation.

$$I(t)=Ir+Is+2\sqrt{Ir \cdot Is} \cos [\varphi_0(t)+\varphi_{UT}(t)] \quad \text{[Eq. 1]}$$

Ir represents the photocurrent by reference light Pr. Is represents the photocurrent by signal light Ps. $\varphi_0(t)$ represents a phase difference between the reference light and the signal light when no ultrasound-induced displacement occurs. $\varphi_{UT}(t)$ represents a phase change caused by ultrasound-induced displacement.

The Michelson interferometer illustrated in FIG. 1 includes a laser 1, a beam splitter 2, a reflecting mirror 4, and a photodetector 5. The laser 1 irradiates a specimen 3 with laser light.

The light emitted from the laser 1 is split into two beams by the beam splitter 2. One of the beams is directed to the specimen 3 as incident light PI, while the other is directed to the reflecting mirror 4. The light PI impinges on the specimen 3, which is then reflected off the specimen 3. Subsequently, the reflected light (signal light) Ps is transmitted through the beam splitter 2. The light (reference light) that has been transmitted through the beam splitter 2 is reflected off the reflecting mirror 4 and then reflected off the beam splitter 2. Subsequently, the light (reference light) is combined with the signal light Ps into a combined wave, which is then directed to the photodetector 5.

Figure 2:
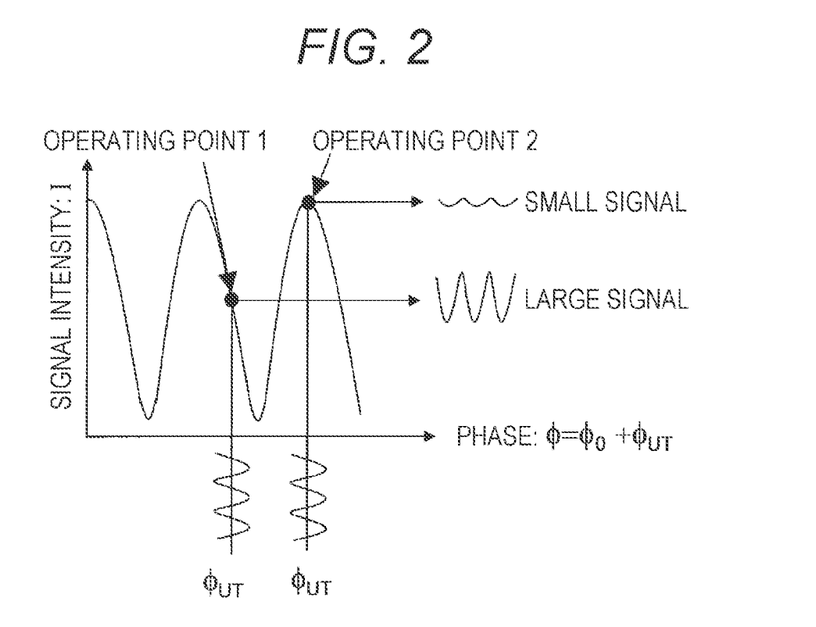
FIG. 2 is a schematic graph illustrating a relationship between a signal intensity and a phase when the Michelson interferometer in FIG. 1 is used.

In this case, as illustrated in FIG. 2, the amplitude of the signal intensity I(t) largely depends on an operating point $\varphi_0(t)$. The signal is at maximum when the operating point is at $\pm\pi/2+2n\pi$ (n is an integer) (operating point 1), and the signal is small at another point (operating point 2). Under such circumstances, the detection sensitivity needs to be increased by amplifying the signal light without increasing the power of laser with which the specimen 3 is to be irradiated.

In this regard, JP-2014-109481-A described above discloses a polarizing beam splitter 106 as a splitting means for splitting laser light. However, no description is given of the amplification of signal light without increasing the power of laser with which a specimen is to be irradiated.

In addition, JP-2014-160057-A described above discloses a polarizing beam splitter 404 as a splitting means for splitting laser light. However, no description is given of the amplification of signal light without increasing the power of laser with which a specimen is to be irradiated.

The present invention has been made to solve the above-described issue of the related art. An object of the present invention is to provide a laser measuring device and a laser ultrasonic device capable of measuring a specimen with high sensitivity by irradiating the specimen with laser light without increasing the power of the light with which the specimen is to be irradiated.

A laser measuring device according to one aspect of the present invention includes a light source configured to emit laser light, a first splitter configured to split the laser light into light to be incident on a specimen and reference light that travels in a predetermined direction, a second splitter on which a combined wave is incident, the combined wave formed by combining signal light reflected off the specimen and the reference light traveling in a direction different from the predetermined direction, a first photodetection unit configured to detect one part of the combined wave that has been transmitted through the second splitter, and a second photodetection unit configured to detect another part of the combined wave that has been reflected off the second splitter. The first splitter has an asymmetric splitting ratio set such that power of the reference light becomes larger than power of the light to be incident on the specimen.

A laser ultrasonic device according to another aspect of the present invention includes a transmission unit configured to irradiate the specimen with transmission laser light and a reception unit including the laser measuring device.

According to the present invention, it is possible to measure a specimen with high sensitivity by irradiating the specimen with laser light without increasing the power of the light with which the specimen to be irradiated.

DESCRIPTION OF THE PREFERRED EMBODIMENTS

Embodiments of the present invention will be described in detail below with reference to the drawings.

First Embodiment

Figure 3:
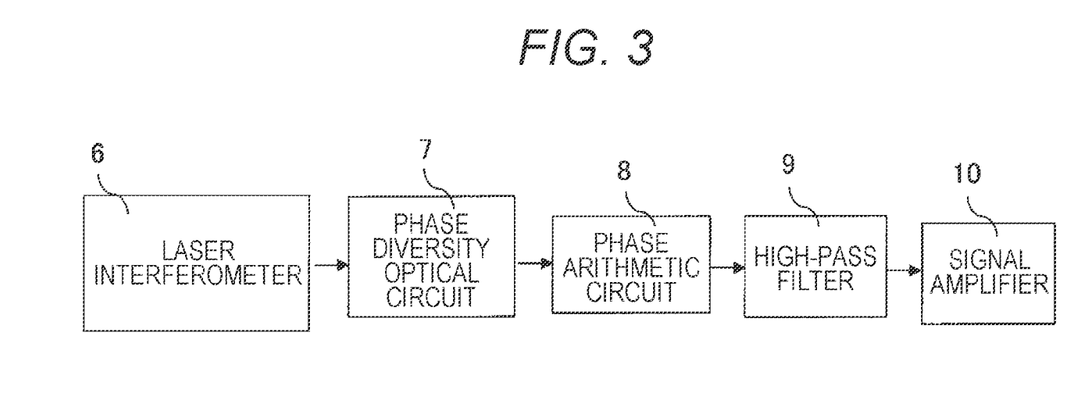
FIG. 3 is a block diagram of a laser measuring device (a laser interferometric displacement gauge) according to a first embodiment of the present invention.
Figure 4:
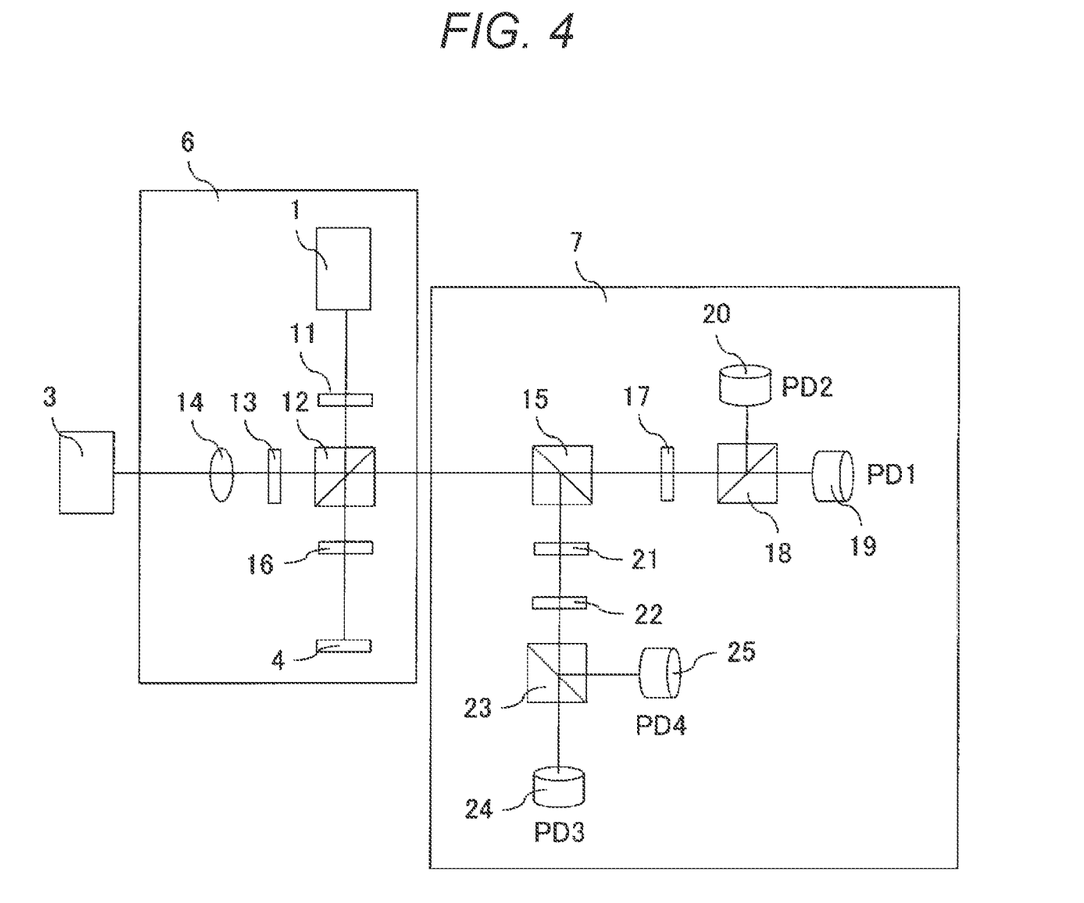
FIG. 4 is a block diagram of the laser measuring device (a laser interferometer and a phase diversity optical circuit) according to the first embodiment of the present invention.

The following describes a laser measuring device according to the first embodiment of the present invention with reference to FIGS. 3 and 4.

FIG. 3 is a block diagram illustrating an overall configuration for realizing the laser measuring device (laser interferometric displacement gauge) according to the first embodiment of the present invention. The laser measuring device includes a laser interferometer 6, a phase diversity optical circuit 7, a phase arithmetic circuit 8, a high-pass filter 9 (low frequency component removing unit), and a signal amplifier 10.

The following describes the laser interferometer 6 and the phase diversity optical circuit 7 included in the laser measuring device with reference to FIG. 4. Although a Michelson interferometer is used as an interferometer in the first embodiment, a Mach-Zehnder interferometer may also be used.

In the first embodiment described above, the laser measuring device (the laser interferometer 6 and the phase diversity optical circuit 7) includes a light source 1, a first splitter (a polarizing beam splitter 12), a second splitter (a beam splitter 15), first photodetection units (photodetectors 19 and 20), and second photodetection units (photodetectors 24 and 25). The light source 1 emits laser light. The first splitter (the polarizing beam splitter 12) splits the laser light into light to be incident on a specimen 3 and reference light that travels in a predetermined direction. Signal light reflected off the specimen 3 and the reference light traveling in a direction different from the predetermined direction combine together, forming a combined wave which is then incident on the second splitter (the beam splitter 15). The first photodetection units (photodetectors 19 and 20) detect one part of the combined wave that has been transmitted through the second splitter (the beam splitter 15). The second photodetection units (photodetectors 24 and 25) detect another part of the combined wave that has been reflected off the second splitter (the beam splitter 15). The first splitter (the polarizing beam splitter 12) has an asymmetric splitting ratio set such that the power of the reference light becomes larger than the power of light to be incident on the specimen 3. With such a configuration, the signal light from the specimen 3 can be measured with high sensitivity without increasing the power of the light with which the specimen 3 is to be irradiated.

Specifically, the light emitted from the light source 1 is transmitted through a first $\lambda/2$ plate 11, through which the polarization direction is rotated by 45 degrees. The first polarizing beam splitter 12 splits the rotated polarized light into two beams of linearly polarized light orthogonal to each other, one of which becomes incident light to be incident on the specimen 3 and the other becomes reference light.

As described above, the first polarizing beam splitter 12 (the first splitter) has an asymmetric splitting ratio set such that the power of the reference light becomes larger than the power of the incident light. This asymmetric splitting ratio is preferably enlarged to, for example, 10:1.

One beam of the polarized light that has been reflected is transmitted through a first $\lambda/4$ plate 13, and then converted into circularly polarized light. Subsequently, the light is collected by a condenser lens 14, and the specimen 3 is irradiated with the light. The reflected light (signal light) from the specimen 3 is turned into parallel light again by the condenser lens 14, and then into linearly polarized light by the first $\lambda/4$ plate 13. However, since the rotation direction of the circularly polarized light is reversed by the reflection on the specimen 3, the direction of the linearly polarized light is orthogonal to the direction of the original light. Accordingly, the signal light is transmitted through the first polarizing beam splitter 12 (the first splitter) and then directed to the beam splitter 15 (the second splitter).

The light (reference light) in the polarization direction that has been transmitted through the first polarizing beam splitter 12 is transmitted through a second $\lambda/4$ plate 16, converted into circularly polarized light, and then reflected off a reflecting mirror 4. As with the signal light, the reference light is converted into linearly polarized light, which is orthogonal to the original reference light, by the second $\lambda/4$ plate 16. Accordingly, the reference light is reflected off the first polarizing beam splitter 12 and combined with the signal light, which is then directed to the beam splitter 15.

At this time, the signal light and the reference light are combined together in a state in which the polarization directions are orthogonal to each other. One part of the combined wave is transmitted through a half mirror, i.e., the beam splitter 15, and the polarization direction thereof is rotated by 45 degrees by a second λ/2 plate 17. Subsequently, a polarizing beam splitter 18 splits the light into beams of linearly polarized light orthogonal to each other, which are then detected by respective photodetectors, i.e., a first photodetector 19 (PD1) and a second photodetector 20 (PD2).

The photodetector PD1 detects a projection component in the P polarization direction of the reference light Er and the signal light Es. The photodetector PD2 detects a projection component in the S polarization direction of the reference light Er and the signal light Es. The signals detected by the photodetectors PD1 and PD2 are as expressed by the following equations 2 and 3, respectively.

$$I_{PD1} = \left| \frac{1}{2}Es + \frac{1}{2}Er \right|^2 = \frac{1}{4}|Es|^2 + \frac{1}{4}|Er|^2 + \frac{1}{2}|Es||Er|\cos[\phi s - \phi r] \quad [\text{Eq. 2}]$$

$$I_{PD2} = \left| \frac{1}{2}Es - \frac{1}{2}Er \right|^2 = \frac{1}{4}|Es|^2 + \frac{1}{4}|Er|^2 - \frac{1}{2}|Es||Er|\cos[\phi s - \phi r] \quad [\text{Eq. 3}]$$

Another part of the combined wave is reflected off the half mirror, i.e., the beam splitter 15, and given a phase difference of 90 degrees between the signal light and the reference light by a third λ/4 plate 21. Subsequently, the polarization direction thereof is rotated by 45 degrees by a third λ/2 plate 22. A beam splitter 23 then splits the light into beams of linearly polarized light orthogonal to each other, which are then detected by respective photodetectors, i.e., a third photodetector 24 (PD3) and a fourth photodetector 25 (PD4). In a state where there is a phase difference of 90 degrees between Er and Es, the signals detected by the photodetectors PD3 and PD4 are as expressed by the following equations 4 and 5, respectively.

$$I_{PD3} = \frac{1}{8}|(1-j)Es + (1+j)Er|^2 = \quad [\text{Eq. 4}]$$
$$\frac{1}{4}|Es|^2 + \frac{1}{4}|Er|^2 + \frac{1}{2}|Es||Er|\sin[\phi s - \phi r]$$

$$I_{PD4} = \frac{1}{8}|(1+j)Es + (1-j)Er|^2 = \quad [\text{Eq. 5}]$$
$$\frac{1}{4}|Es|^2 + \frac{1}{4}|Er|^2 - \frac{1}{2}|Es||Er|\sin[\phi s - \phi r]$$

(1+j) and (1−j) in the equations 4 and 5 indicate that Es and Er are given a phase difference of ±45 degrees (a difference of 90 degrees) by the third λ/4 plate 21. Here, j represents an imaginary unit.

Next, differential signals are taken between PD1 and PD2 and between PD3 and PD4, as expressed in their respective equations 6 and 7.

$$S1 = I_{PD1} - I_{PD2} = |Es||Er|\cos[\varphi s - \varphi r] \quad [\text{Eq. 6}]$$

$$S2 = I_{PD3} - I_{PD4} = |Es||Er|\sin[\varphi s - \varphi r] \quad [\text{Eq. 7}]$$

The resultant signals are, therefore, in the shape of the product of the signal light amplitude intensity and the reference light amplitude intensity. These equations indicate that increasing the intensity of the reference light (|Er|) can generate a large signal output. The terms of cosine and sine are multiplied in the respective equations 6 and 7. Each of the terms represents a phase difference between the signal light and the reference light. However, since the optical path lengths of the reference light and the signal light change constantly due to environmental vibration and the like, the phase terms of the equations 6 and 7 remain unfixed, changing signals S1 and S2 significantly.

These are, therefore, subjected to a division operation using the equations 6 and 7, after which an arctangent function operation is performed to obtain a signal (the phase arithmetic circuit 8) in the embodiment of the present invention.

$$\phi s - \phi r = \tan^{-1}\left[\frac{S2}{S1}\right] = \tan^{-1}\left[\frac{\sin[\phi s - \phi r]}{\cos[\phi s - \phi r]}\right] \quad [\text{Eq. 8}]$$

By performing the operations in this way, it is possible to obtain the phase difference itself between the signal light and the reference light, which allows the obtainment of a constant signal in a stable and assured manner. In a case where the signal intensities of the signals S1 and S2 are equal to or lower than the noise levels of the photodetectors on which respective signals are incident, the signal-to-noise ratio (SN ratio) is deteriorated. However, as is obvious from the equations 6 and 7, the signals S1 and S2 can be amplified by increasing the reference light (|Er|).

By increasing the reference light, therefore, the SN ratio can be improved according to the embodiment of the present invention. A similar effect can also be obtained by increasing the signal light (|Es|) with the equations 6 and 7. For the amplification of the signal light, however, the power of the light to be incident on the specimen 3 needs to be increased. In this case, a new ultrasonic signal may be generated in the specimen 3.

In a case where the laser measuring device (laser interferometric displacement gauge) according to the embodiment of the present invention serves as a receiver of a laser ultrasonic device, ultrasound generated by the laser for the receiver in addition to ultrasound induced by the transmission laser may cause a noise.

Furthermore, in a case where the laser measuring device (laser interferometric displacement gauge) according to the embodiment of the present invention is made into an optical fiber probe, the increased power of the incident light may damage the optical fiber. Therefore, the laser measuring device (laser interferometric displacement gauge) according to the embodiment of the present invention is capable of amplifying a desired signal not by increasing the power of the light to be incident on the specimen 3, but by increasing the power of the reference light.

Subsequently, the phase time-changing signal obtained with the equation 8 is input into the high-pass filter 9. The high-pass filter 9, capable of transmitting a frequency (100 KHz or higher) component of the ultrasound, removes a phase change component (100 KHz or lower) included due to an environmental-vibration induced change in the optical path difference between the signal light and the reference light. Finally, a signal output from the high-pass filter 9 is amplified to a desired level by the signal amplifier 10.

Second Embodiment

Figure 5:
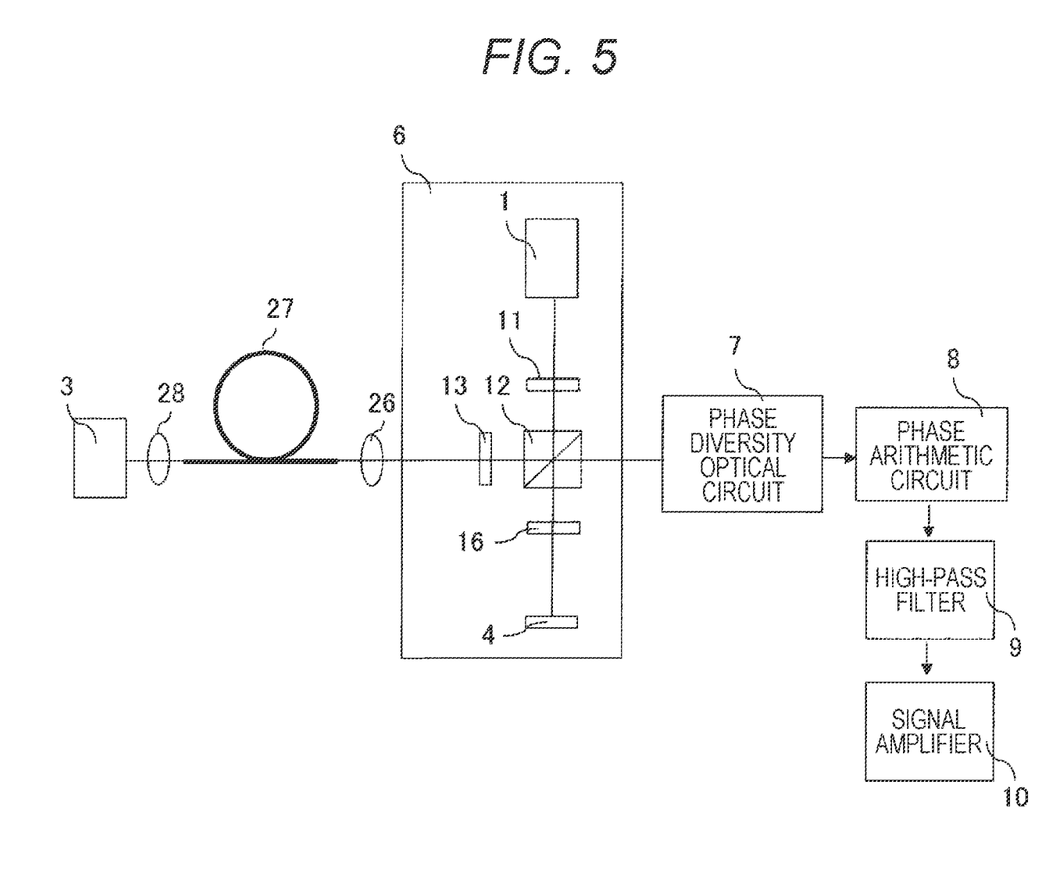
FIG. 5 is a block diagram of a laser measuring device of an optical fiber probe type according to a second embodiment of the present invention.

The following describes a laser measuring device according to the second embodiment of the present invention with reference to FIG. 5. FIG. 5 is a schematic diagram of the laser measuring device (laser interferometric displacement gauge) of the optical fiber probe type.

Incident light from a laser interferometer 6 is collected by a condenser lens 26 and then launched into a polarization-maintaining optical fiber 27. The light emitted from the polarization-maintaining optical fiber 27 is collected by a condenser lens 28, and a specimen 3 is irradiated with the light.

As in the first embodiment, signal light and reference light from the laser interferometer 6 enter a phase diversity optical circuit 7, after which a signal is obtained through a phase arithmetic circuit 8, a high-pass filter 9, and a signal amplifier 10. Generally, aligning the optical axis of an optical system is difficult with the laser interferometer 6. However, the polarization-maintaining optical fiber 27 made into a probe obviates the need for the alignment of the optical axis.

As described in the first embodiment, the laser measuring device (laser interferometric displacement gauge) according to the embodiment of the present invention is capable of amplifying a signal just by increasing the power of the reference light, and there is no need to increase the power of the light with which the specimen 3 is to be irradiated. With this configuration, the polarization-maintaining optical fiber 27 can be made into a probe easily, since the polarization-maintaining optical fiber 27 is not damaged by high-power light that would otherwise enter the polarization-maintaining optical fiber 27.

Third Embodiment

Figure 6:
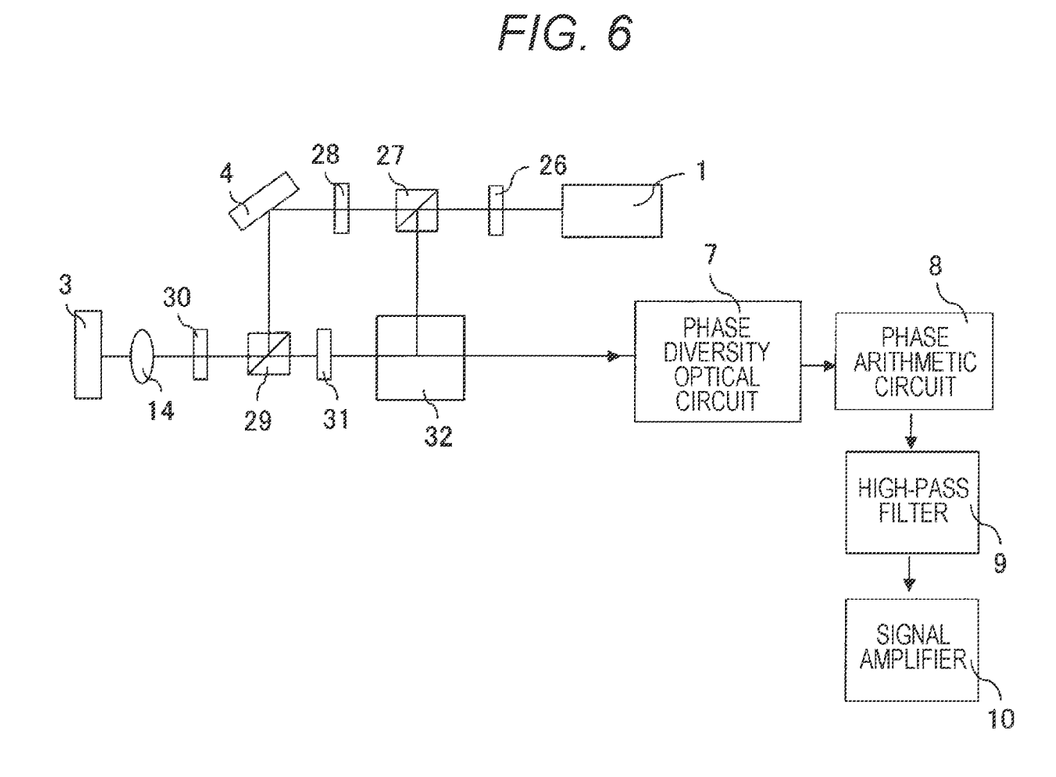
FIG. 6 is a block diagram of a laser measuring device according to a third embodiment of the present invention, in which a two-wave mixing element is used.

The following describes a laser measuring device according to the third embodiment of the present invention with reference to FIG. 6.

In FIG. 6, the laser measuring device (laser interferometric displacement gauge) according to the third embodiment of the present invention is illustrated. The laser measuring device (laser interferometric displacement gauge) according to the third embodiment of the present invention includes a mechanism that causes wavefronts of reference light and signal light to be identical by using a two-wave mixing element. The mechanism for causing the wavefront of the reference light to be identical to the wavefront of the signal light using the two-wave mixing element is described in R. J. Dewhurst, et al., "Optical remote measurement of ultrasound", Meas. Sci. Technol., vol. 10, pp. 139-168 (1999) described above.

For the case of a specimen 3 having a rough surface, the reflected light (signal light) from the specimen 3 is scattered, whereby the wavefront of the signal light is different from the wavefront of the plane wave of the reference light. The difference between the wavefronts weakens the interference effect between the reference light and the signal light. Accordingly, by using the method disclosed in R. J. Dewhurst, et al., "Optical remote measurement of ultrasound", Meas. Sci. Technol., vol. 10, pp. 139-168 (1999) described above, the wavefront of the reference light can be matched with the wavefront of the signal light scattered.

By applying, to the embodiment of the present invention, the method disclosed in R. J. Dewhurst, et al., "Optical remote measurement of ultrasound", Meas. Sci. Technol., vol. 10, pp. 139-168 (1999) described above, it is possible to provide a laser interferometric displacement gauge capable of measuring, with high sensitivity, even a specimen having a rough surface.

The following describes a configuration of the laser measuring device according to the third embodiment of the present invention with reference to FIG. 6.

The light emitted from a laser 1 passes through a $\lambda/2$ plate 26. Then, a polarizing beam splitter 27 (a first splitter) splits the light at an asymmetric ratio, by which the power of light (reference light) reflected off the polarizing beam splitter 27 becomes larger than the power of light being transmitted therethrough. The light transmitted through the polarizing beam splitter 27 passes through a $\lambda/2$ plate 28, and the optical path thereof is changed by 90 degrees by a reflecting mirror 4. After the light is reflected off a polarizing beam splitter 29, the light is transmitted through a $\lambda/4$ plate 30 and collected by a condenser lens 14. The specimen 3 is then irradiated with the light. The reflected light (signal light) scattered by the specimen 3 again turns into parallel light by the condenser lens 14, which is then transmitted through the $\lambda/4$ plate 30, the polarizing beam splitter 29, and a $\lambda/2$ plate 31. The light is then incident on a two-wave mixing element 32.

As the materials of the two-wave mixing element 32, it is preferable to use a ferroelectric oxide such as lithium niobate ($LiNbO_3$), lithium tantalate ($LiTaO_3$), and barium titanate ($BaTiO_3$) or a quantum well compound semiconductor such as InGaAs/GaAs, which are photorefractive materials.

The light (reference light) reflected off the polarizing beam splitter 27 is incident on the two-wave mixing element 32, and the wavefront of the reference light is converted to the wavefront of the signal light through a photorefractive effect induced by the signal light in the two-wave mixing element 32. As a result, the wavefront of the reference light becomes identical to the wavefront of the signal light, after which the light is incident on a phase diversity optical circuit 7. The other operations are similar to those in the first embodiment described above, and thus the description thereof will be omitted.

Fourth Embodiment

Figure 7:
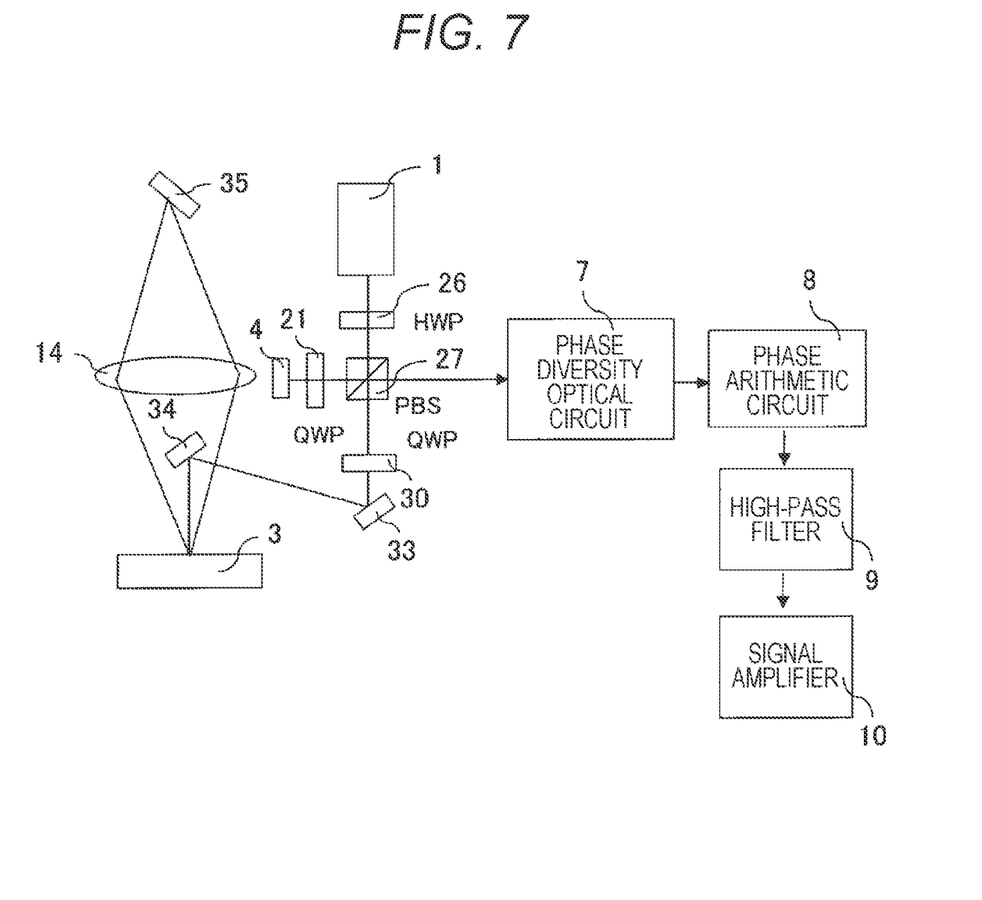
FIG. 7 is a block diagram of a laser measuring device according to a fourth embodiment of the present invention, in which a phase conjugate mirror is used.

The following describes a laser measuring device according to the fourth embodiment of the present invention with reference to FIG. 7.

In FIG. 7, the laser measuring device (laser interferometric displacement gauge) according to the fourth embodiment of the present invention is illustrated. The laser measuring device (laser interferometric displacement gauge) according to the fourth embodiment of the present invention includes a mechanism that causes a wavefront of signal light to be identical to a wavefront of reference light by using a phase conjugate mirror. The mechanism for causing the wavefront of the signal light to be identical to the wavefront of the reference light using a phase conjugate mirror 35 is described in R. J. Dewhurst, et al., "Optical remote measurement of ultrasound", Meas. Sci. Technol., vol. 10, pp. 139-168 (1999).

For the case of a specimen 3 having a rough surface, the reflected light (signal light) from the specimen 3 is scattered, whereby the wavefront of the signal light is different from the wavefront of the plane wave of the reference light. The difference between the wavefronts weakens the interference effect between the reference light and the signal light. Accordingly, by using the method disclosed in R. J. Dewhurst, et al., "Optical remote measurement of ultrasound", Meas. Sci. Technol., vol. 10, pp. 139-168 (1999), the wavefront of the signal light scattered can be matched with the wavefront (that is, a plane wave) of the reference light. By applying, to the embodiment of the present invention, the method disclosed in R. J. Dewhurst, et al., "Optical remote measurement of ultrasound", Meas. Sci. Technol., vol. 10, pp. 139-168 (1999), it is possible to provide a laser measuring device (laser interferometric displacement gauge) capable of measuring, with high sensitivity, even the specimen 3 having a rough surface.

The following describes in detail a configuration of the laser measuring device according to the fourth embodiment of the present invention with reference to FIG. 7.

The light emitted from a laser 1 passes through a λ/2 plate 26. Then, a polarizing beam splitter 27 (a first splitter) splits the light at an asymmetric ratio, by which the power of light (reference light) reflected off the polarizing beam splitter 27 becomes larger than the power of light being transmitted therethrough. The light transmitted through the polarizing beam splitter 27 passes through a λ/4 plate 30. Subsequently, the optical path thereof is changed by a reflecting mirror 33, and further changed by a reflecting mirror 34. A specimen 3 is then irradiated with the light. Subsequently, the reflected light (signal light) scattered by the specimen 3 is incident on the phase conjugate mirror 35 through a condenser lens 14.

As the materials of the phase conjugate mirror 35, it is preferable to use a ferroelectric oxide such as lithium niobate ($LiNbO_3$), lithium tantalate ($LiTaO_3$), and barium titanate ($BaTiO_3$) or a quantum well compound semiconductor such as InGaAs/GaAs, which are photorefractive materials.

The signal light reflected from the phase conjugate mirror 35 passes through the condenser lens 14, the specimen 3, the reflecting mirror 34, the reflecting mirror 33, and the λ/4 plate 30. The signal light is then reflected off the polarizing beam splitter 27. At this time, the wavefront of the signal light is converted from the wavefront of the scattered light into the plane wave, whereby the wavefront of the signal light becomes identical to the wavefront of the reference light.

The light (reference light) reflected off the polarizing beam splitter 27 passes through a λ/4 plate 21. The light is then reflected off a reflecting mirror 4, passes through the λ/4 plate 21 again, and further through the polarizing beam splitter 27. Subsequently, the light is incident on a phase diversity optical circuit 7 together with the signal light turned into the plane wave again. The other operations are similar to those in the first embodiment described above, and thus the description thereof will be omitted.

Fifth Embodiment

Figure 8:
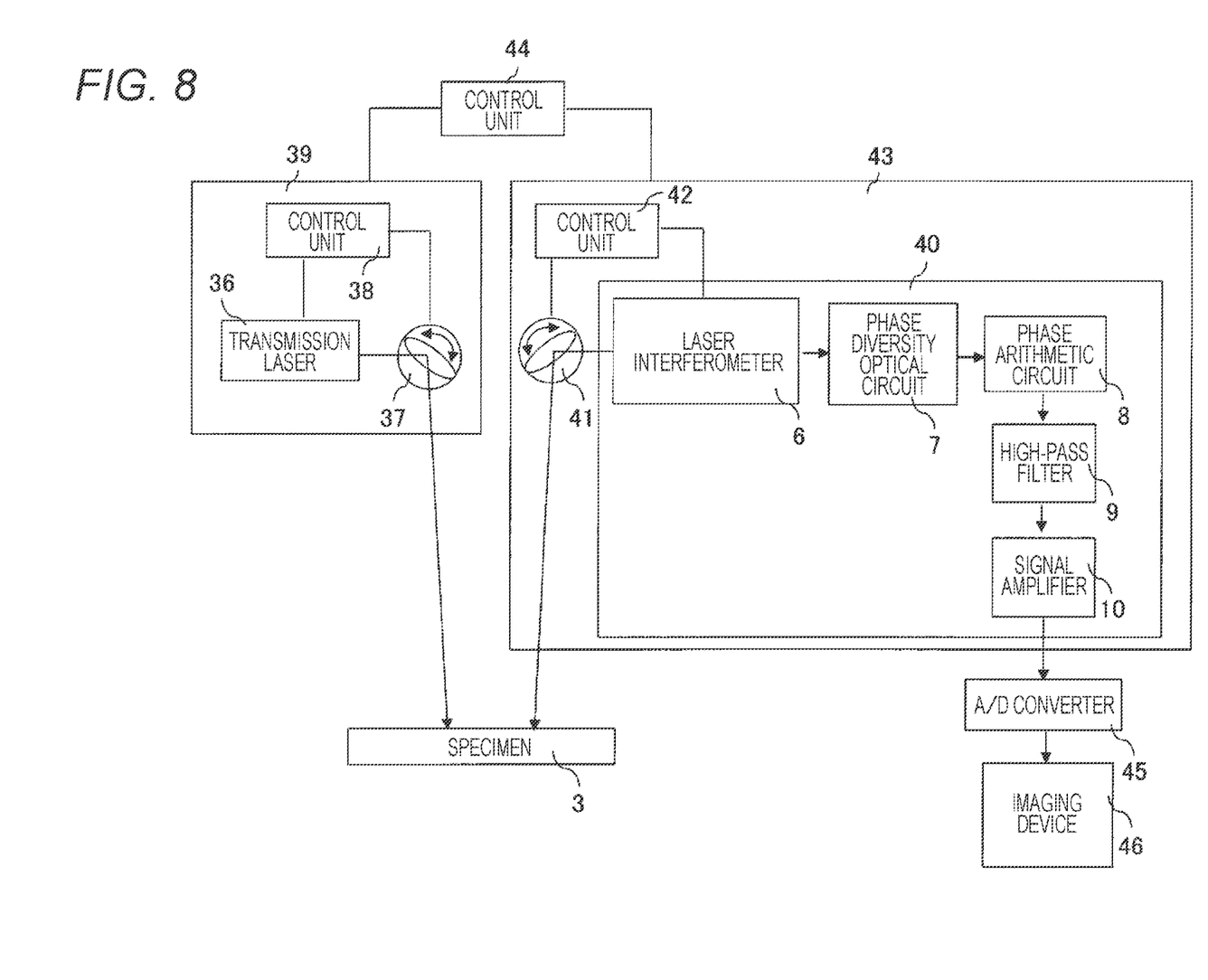
FIG. 8 is a configuration diagram of a laser ultrasonic device according to a fifth embodiment of the present invention, in which a laser measuring device is used.

The following describes a laser ultrasonic device according to the fifth embodiment of the present invention with reference to FIG. 8.

The laser ultrasonic device according to the fifth embodiment illustrated in FIG. 8 is a laser ultrasonic device including the laser measuring device (laser interferometric displacement gauge 40) according to the first embodiment illustrated in FIG. 3. A basic configuration illustrated herein is described in Y. K. An., et al., "Complete noncontact laser ultrasonic imaging for automated crack visualization in a plate", Smart Mater. Struct., vol. 22, pp. 1-10 (2013).

The laser ultrasonic device according to the fifth embodiment includes a transmission unit 39, a reception unit 43, a control unit 44, an analog-to-digital (A/D) converter 45, and an imaging device (image forming unit) 46. The transmission unit 39 includes a transmission laser 36, a galvanometer mirror 37, and a control unit 38. The galvanometer mirror 37 scans transmission laser light. The control unit 38 is for synchronizing the transmission laser 36 and the galvanometer mirror 37.

The reception unit 43 includes a reception laser 1 for the laser measuring device (laser interferometric displacement gauge 40) according to the embodiment of the present invention, a galvanometer mirror 41, and a control unit 42. The galvanometer mirror 41 scans the laser light. The control unit 42 is for synchronizing the reception laser 1 and the galvanometer mirror 41. The transmission unit 39 and the reception unit 43 are synchronized by the control unit 44. An output from the reception unit 43 is converted from an analog signal into a digital signal by the A/D converter 45, and then a detection image is formed by the imaging device 46.

As described above, according to the embodiments of the present invention, it is possible to amplify the signal light and increase the detection sensitivity without increasing the power of the laser with which the specimen is to be irradiated. Furthermore, since the displacement of the specimen induced by ultrasound is detected as a phase difference between the reference light and the signal light, it is possible to detect the signal light in a stable manner, without depending on a phase difference between the reference light and the signal light which is caused by a factor (e.g., environmental vibration) other than the ultrasound.

Although the invention made by the inventor has been concretely described on the basis of the embodiments, the present invention is not limited to the above-described embodiments, and various modifications can be made without departing from the gist of the present invention.

What is claimed is:

1. A laser measuring device comprising:
   a light source configured to emit laser light;
   a first splitter configured to split the laser light into light to be incident on a specimen and reference light that travels in a predetermined direction;
   a second splitter on which a combined wave is incident, the combined wave formed by combining signal light reflected off the specimen and the reference light traveling in a direction different from the predetermined direction;
   a third splitter on which a first part of the combined wave transmitted through the second splitter is incident;
   a fourth splitter on which a second part of the combined wave split reflected off the second splitter is incident;
   a first photodetection unit which includes a first single beam photodetector configured to detect a first component of the first part of the combined wave that has been transmitted through the third splitter and a second single beam photodetector configured to detect a second component of the first part of the combined wave that has been reflected off the third splitter; and
   a second photodetection unit which includes a third single beam photodetector configured to detect a first component of the second part of the combined wave that has been transmitted through the fourth splitter and a fourth single beam photodetector configured to detect a second component of the second part of the combined wave that has been reflected off the fourth splitter;
   wherein the first splitter has an asymmetric splitting ratio set such that power of the reference light is larger than power of the light to be incident on the specimen, and
   wherein the asymmetric splitting ratio of the first splitter is set such that the power of the light to be incident on the specimen does not generate ultrasound on the specimen and destroy the specimen.

2. The laser measuring device according to claim 1, further comprising:
a phase arithmetic circuit configured to obtain a phase difference between the signal light and the reference light by performing a predetermined operation using outputs from the first single beam photodetector, the second single beam photodetector, the third single beam photodetector, and the fourth single beam photodetector,
wherein a phase difference between the signal light and the reference light is set to 180° between the first single beam photodetector and the second single beam photodetector, 180° between the third single beam photodetector and the fourth single beam photodetector, and 90° between the first single beam photodetector and the third single beam photodetector.

3. The laser measuring device according to claim 2, wherein the phase arithmetic circuit is configured to perform a division operation between a first differential signal obtained between the outputs of the first single beam photodetector and the second single beam photodetector and a second differential signal obtained between the third single beam photodetector and the fourth single beam photodetector.

4. The laser measuring device according to claim 3, wherein the phase arithmetic circuit is further configured to perform an arctangent function operation with respect to a result of the division operation to obtain the phase difference between the signal light and the reference light.

5. The laser measuring device according to claim 4, further comprising:
a filter configured to remove a phase change component included due to a change in an optical path difference between the signal light and the reference light caused by environmental vibration.

6. The laser measuring device according to claim 5, further comprising:
a signal amplifier configured to amplify an output signal from the filter to a predetermined level.

7. The laser measuring device according to claim 1, wherein the light split by the first splitter and to be incident on the specimen is incident on an optical fiber before being incident on the specimen, and beams of light emitted from the optical fiber are collected and incident on the specimen.

8. The laser measuring device according to claim 7, wherein the asymmetric splitting ratio of the first splitter is set so as not to damage the optical fiber.

9. The laser measuring device according to claim 1, further comprising:
a mechanism configured to cause a wavefront of the reference light to be identical to a wavefront of the signal light using a two-wave mixing element.

10. The laser measuring device according to claim 1, further comprising:
a mechanism configured to cause a wavefront of the signal light to be identical to a wavefront of the reference light using a phase conjugate mirror.

11. The laser measuring device according to claim 1, wherein the asymmetric splitting ratio is set so as to increase the power of the reference light, while not increasing the power of the light to be incident on the specimen.

12. A laser ultrasonic device comprising:
a transmission unit configured to irradiate a specimen with transmission laser light; and
a reception unit including the laser measuring device according to claim 1.

13. The laser ultrasonic device according to claim 12, further comprising:
a control unit configured to synchronize the transmission unit and the reception unit;
an analog-to-digital (A/D) converting unit configured to convert an output of the reception unit from an analog signal into a digital signal; and
an image forming unit configured to receive the digital signal converted by the A/D converting unit and form a detection image.

14. The laser ultrasonic device according to claim 12, wherein the transmission unit includes:
a transmission laser;
a first mirror configured to scan laser light of the transmission laser; and
a first control unit configured to synchronize the transmission laser and the first mirror, and
the reception unit includes:
a reception laser for the laser measuring device;
a second mirror configured to scan laser light of the reception laser; and
a second control unit configured to synchronize the reception laser and the second mirror.

* * * * *